United States Patent [19]

Wikel

[11] Patent Number: 5,344,645
[45] Date of Patent: Sep. 6, 1994

[54] IMMUNOGENS DERIVED FROM PATHOGEN-FREE TICK SPECIES OR CELL LINES, AND TICK VACCINES DERIVED THEREFROM

[75] Inventor: Stephen K. Wikel, Stillwater, Okla.

[73] Assignee: Center for Innovation and Business Development Foundation, Grand Forks, N. Dak.

[21] Appl. No.: 673,671

[22] Filed: Mar. 22, 1991

[51] Int. Cl.$^5$ .................. A61K 39/00; C07K 15/08
[52] U.S. Cl. ...................... 424/265.1; 530/350; 424/184.1
[58] Field of Search .................. 424/88, 85.8; 530/350

[56] References Cited

U.S. PATENT DOCUMENTS 4,814,170  3/1989  Karr, Jr. .......................... 424/85.8

OTHER PUBLICATIONS

Rand et al. Cloning and Expression of a productive antigen . . . PNAS:86, 9657–9661, 1989.
Wikel, S. K. 1984. "Tick and Mite Toxicosis And Allery", *Handbook of Natural toxins.* vol. 2 Insect Poisons, Allergens and Other Invergebrate Venoms. A. T. Ut, Editor. Marcel Dekker. New York, N.Y., pp. 371–396.
Wikel, S. K. 1984. "Immunodulation of Host Responses to Ectoparasite Infestation", *Veterinary Parasitology* 14: 329–339.
George, J. E., Osburn, R. L. and Wikel, S. K. 1985. "Acquisition And Expression of Resistances by *Bos indicus* and *Bos indicus* × *Bos tarus* calves to *Amblyomma americanum* infestation", *Journal of Parasitology.* 71: 174–182.
Wikel, S. K. 1985, "Effects of Tick Infestation on the Plaaug–Forming Cell Response To a Thymic Dependent Antigen", *Annals of Tropical Medicine and Parasitology* 79: 195–198.
Wikel, S. K. 1985. "Resistance To Ixodid Tick Infestation Induced By Administration of Tick Tissue Culture Cells", *Annals of Tropical Medicine and Parasitology* 79: 513–518.
Wikel, S. K. and Whelen, A. C. 1986. "Ixodid Tick––Host Immune Interactions of Tick Tissue Culture Cells", *Annals of Tropical Medicine and Parasitology* 20: 149–174.
Whelen, A. C., Richardson, L. K. and Wikel, S. K. 1986. "Dot-ELISA Assessment of Guinea Pig antibody Responses To Repeated *Dermacentor andersoni* infestations", *Journal of Parasitology* 72: 155–162.
Wikel, S. K., Howard, V. M. and Olsen, F. W., Jr. 1986. "Immunological Studies of Ixodid Tick–Host Interaction: Analysis of Immunogens", *Journal of Toxicology, Toxin Reviews* 5:1 145–160.
Wikel, S. K. 1988. "Immunological Control of Hematophagous Arthropod Vectors: Utilization of Novel Antigens", *Veterinary Parasitology* 29: 235–264.
Yunker, C. R. and Meibos, H., 1979. "Cultural of Embryonic Tick Cells (Acari:Ixodidae)", *National Institute of Allergy and Infectious Diseases,* National Institutes of Health, pp. 1015–1017.
Trager, W., "Acquired Immunity To Ticks", *Journal of Parasitology,* 25:57–81 (1939).
Bagnall, B. G., "Cutaneous Immunity To the Tick *Ixodes holocyclus,*" Ph.D. Thesis, University of Sydney, 186 pp (1975).
Brossard, M., "Relations immunogologiques entre bivins et tiques, plus partialierement entre bovins et *Boophilus microplus*", *Acta Tropica* 33:15–36 (1976).
Wikel, S. K., "The Induction of Host Resistance To Tick Infestation With a Slivary Gland Antigen", *American Journal of Tropical Medicine and Hygiene,* 30:284–288 (1981).

(List continued on next page.)

*Primary Examiner*—Kay K. Kim
*Attorney, Agent, or Firm*—Zarley, McKee, Thomte, Voorhees & Sease

[57] ABSTRACT

Immunogens for vaccination of mammals to prevent tick infestation and transfer of disease from ticks to host animals. The immunogens are derived from cells of pathogen-free ticks, preferably tick gut brush border cells or developing larvae cells, and provide positive responses to immunoblotting and cell mediated immune response to the host, and as well do not cause heightened cutaneous response to tick feeding.

21 Claims, No Drawings

OTHER PUBLICATIONS

Wong, J. Y. M. and Opdebeeck, J. P., "Protection Efficacy of Antigens Solubilized From Gut Membranes of the Cattle Tick, *Biophilus microplus*", *Immunology*, 66:149–155 (1989).

Willadsen, P., "Immunological Approaches To the Control of Ticks", *International Journal of Parasitology*, 17:671–677 (1987).

Walladsen, P. et al., "Immunologic Control of a Parasitic Arthropod. Identification of a Protective Antigen From *Boophilus microplus*", *Journal of Immunology*, 143:1346–1351 (1989).

Wikel, S. K., "Acquired Resistance to Ticks. Expression of Resistance by C4 Deficient Guinea Pigs," *American Journal of Tropical Medicine and Hygiene*, 28:586–590 (1979).

Johnson, A. G., "Modulation of the Immune System By Synthetic Polynucleotides," *Springer Seminars in Immunopathology*, 2:149–168 (1979).

Morein, et al., "The ISCOM: An Immunostimulating Complex," *Immunology Today*, 8:333–338 (1987).

Houck et al., "Isolation and Characterization of Brush Border Fragments From Mosquito Mesenterons," *Archives of Insect Biochemistry and Physiogy*, 3:135–146 (1986).

Thomas and McNamee, "Purification of Membrane Proteins," *Methods in Enzymology*, 182:499–520 (1990).

Laemmli, U. K., "Cleavage of Structural Proteins During Assembly of the Head of Bacteriophase T4," *Nature* 227:680–685 (1970).

O'Farrell et al., "High Resolution Two-Dimensional Gel Electrophoresis of Basic as Well as Acidic Proteins," *Cell*, 12:1133–1142 (1977).

Morrissey, J. H., "Silver Strains for Proteins in Polyacrylamide Gels: A Modified Procedure With Enhanced Uniform Sensitivity," *Analytical Biochemistry*, 117–307:310 (1981).

Opdebeeck, et al., "Hereford cattle immunized and protected against *Boophilus microplus* with soluble and Membrane-associated antigens from the midgut of ticks", *Parasite Immunology* 10: 405–410 (1988).

Bradford, M. M., "A Rapid And Sensitive Method for Quantitation of Microgram Quantities of Protein Utilizing the Principle of Protein Dye-Binding," *Analytical Biochemistry*, 72:248–254 (1976).

Smith, et al., "Measurement of Protein Using Bicinchonicic Acid," *Analytical Biochemistry*, 150:76–85 (1985).

Voller et al., "Enzyme Immunoassays With Special Reference to ELISA Techniques", *Journal of Clinical Pathology*, 31–507–520 (1978).

Lotan, R. and Nicolson, G. L., "Purification of Cell Membrane Glycoproteins: Lectin Affinity Chromatography," *Biochmica et Biophysica Acta*, 559:329–376 (1979).

Young and Lamb, "T Lymphocytes Respond To Solid Phase Antigen: A Novel Approach to the Molecular Analysis of Cellular Immunity," *Immunology*, 59: 167–171 (1986).

Sluyterman and Elgersma, "Chromatofocusing: Isoelectric Focusing on Ion-Exchange Columns. I. General Principles," *Journal of Chromatography*, 150: 17–30 (1978).

Sluyterman and Wijdenes, "Chromatofocusing: Isoelectric Focusing On Ion-Exchange Columns. II. Experimental Verification," *Journal of Chromatography* 150: 31–44 (1978).

Tracy et al., "Development of Monoclonal Antibodies To Proteins Separated By Two-Dimensional Gel Electrophorsis," *Journal of Immunological Methods* 65:97–107 (1983).

Galfre and Milstein, "Preparation of Monoclonal Antibodies: Strategies and Procedures", *Methods in Enzymology*, 73:1–46 (1981).

Hawkes et al., "A Dot-Immunobinding Assay for Monoclonal And Other Antibodies," *Analytical Biochemistry*, 119:142–147 (1982).

McKinney and Parkinson, "A Simple Nonchromatographic Procedure To Purify Immunoglobulins From serum And Ascites Fluid," *Journal of Immunological Methods* 96:271–278 (1987).

Funderud et al., "Fractionation of Lymphocytes By Immunomagnetic Beads," GGB. Klaus, (Ed) IRL Press Oxford, pp. 55–65.

Helenius and Simons, "Solubilization of Membranes By Detergents," *Biochimica et Biophysica Acta*, 415:29–79 (1975).

Brodier, C., "Phase Separation of Integral Membrane Proteins In Triton X-114 Solution," *Journal of Biological Chemistry*, 256:1604–1607 (1981).

Willadsen and Kemp, "Vaccination with 'Concealed' Antigens For Tick Control," *Parasitology Today*, 4:196–198 (1988).

Wong, J. Y. M. and Opdebeeck, J. P., "Protective Efficacy of Antigens Solubilized From Gut Membranes of the Cattle Tick, *Gioophilus microplus,*" *Immunology*, 66:149–155 (1989).

IMMUNOGENS DERIVED FROM PATHOGEN-FREE TICK SPECIES OR CELL LINES, AND TICK VACCINES DERIVED THEREFROM

BACKGROUND OF THE INVENTION

Hematophagous arthropods transmit pathogens of medical and veterinary public health importance, and many of these disease causing agents undergo complex developmental cycles in the vector. Ixodid ticks are the most important arthropod vectors of infectious agents to domestic livestock and wild animals, and they are second to mosquitoes as transmitters of pathogens to humans.

Control of ticks throughout the world is dependent upon acaricides, and broad ranging resistance to these chemicals represents an extremely significant threat to animal health and production, resulting in economic losses to producers and major reductions in food supplies. Acaricide resistance is a global problem involving single and multiple host ticks, and varying degrees of resistance exist for all major chemical groups used for ixodid control.

There are numerous problems associated with chemical control of arthropods. Those include impact of the chemicals on the environment, damage to non-target species and their presence as meat and milk residues. Many of the problems give rise to possible human health implications. These considerations, combined with heightened awareness of an increasing incidence and variety of tick transmitted diseases indicate the need for alternative tick control strategies.

Tick saliva contains pharmacologically active substances and a number of immunogens. Engorgement, that is feeding on host blood, might occur over a period of four to fifteen days. An unfed ixodid female, with a final fed weight of 1000 milligrams, might process 4000 milligrams of host blood, alternating between uptake of blood and salivation every five to 30 seconds. The host can be exposed to a significant quantity and array of immunogenic tick molecules.

Cattle and laboratory animal species acquire resistance to a variety of ixodid species as a consequence of infestation. Impact of acquired resistance is expressed by reduced number of engorged ticks, decreased volume of blood meal, reduced number and viability of ova, increased feeding time, tick death and impaired transmission of pathogens. Cell mediated, antibody and complement dependent effector mechanisms are all part of the complex immunological basis of acquired tick resistance.

Development of immunization induced anti-tick immunity is a logical extension of studies designed to characterize acquired resistance. The first vaccination attempt used an extract of whole *Dermacentor variabilis* larvae as an antigen source (Trager, W., "Acquired Immunity To Ticks," *Journal of Parasitology*, 25:57–81 (1939)). Salivary gland extracts have been used as immunogens to induce host anti-tick immunity that resembled acquired resistance to *Ixodes holocyclus* (Bagnall, B. G., "Cutaneous Immunity To the Ixodid Tick *Ixodes holocyclus*," Ph.D. Thesis, University of Sydney, 186 pp. (1975)), *Boophilus microplus* (Brossard, M., "Relations immunologiques entre bovins et tiques, plus partialierement entre bovins et *Boophilus microplus*, *Acta Tropica* 33:15–36 (1976)); and *Dermacentor andersoni* (Wikel, S. K., "The Induction of Host Resistance To Tick Infestation With a Salivary Gland Antigen", *American Journal of Tropical Medicine and Hygiene*, 30:284–288 (1981)). Immunization with salivary gland immunogens induced variable levels of host resistance and intense cutaneous reactions often developed at tick attachment sites (Wikel, S. K., "Immunological Control of Hematophagous Arthropod Vectors: Utilization of Novel Antigens", *Veterinary Parasitology*, 29:235–264 (1988)). An alternative source of immunogen, which was used to induce significant levels of anti-tick resistance, was primary tick tissue culture cells established from developing larvae (Wikel, S. K., "Resistance To Ixodid Tick Infestation Induced By Administration of Tick Tissue Culture Cells," *Annals of Tropical Medicine and Parasitology*, 79:513–518 (1985)). Vaccination with primary embryo culture cells of *Amblyomma americanum* stimulated significant levels of host immunity not only to *A. americanum*, but also to a challenge infestation with adult *D. andersoni* (Wikel, S. K. (1985) supra).

Recently, anti-tick vaccination studies have focused on "novel" immunogens thought not to be associated with acquired resistance, particularly ixodid digestive tract molecules (Willadsen, P., "Immunological Approaches To the Control of Ticks," *International Journal for Parasitology*, 17:671–677 (1987); Wikel, S. K., "Immunological Control of Hematophagous Arthropod Vectors: Utilization of Novel Antigens," *Veterinary Parasitology*, 29:235–264 (1988)). Reported studies involved development of anti-*B. microplus* (Willadsen, P., "Immunological Approaches To the Control of Ticks," *International Journal for Parasitology*, 17:671–677 (1987); Wong, J. Y. M. and Opdebeeck, J. P., "Protective Efficacy of Antigens Solubilized From Gut Membranes of the Cattle Tick, *Boophilus microplus*," *Immunology*, 66:149–155 (1989)) and anti-*A. americanum* (Wikel, S. K., "Immunological Control of Hematophagous Arthropod Vectors: Utilization of Novel Antigens," *Veterinary Parasitology*, 29:235–264 (1988)) vaccines.

Willadsen, P. et al., "Immunologic Control of a Parasitic Arthropod. Identification of a Protective Antigen From *Boophilus microplus*," *Journal of Immunology*, 143:1346:1351 (1989), using a carefully designed biochemical approach, identified a protection inducing 89.0 kilodalton, kdal., glycoprotein derived from *B. microplus* gut. Variable levels of host resistance were elicited by immunization with this molecule (Willadsen and Kemp, "Vaccination With 'Concealed' Antigens For Tick Control," *Parasitology Today*, 4:196–198 (1988)). A second group investigating bovine resistance to *B. microplus* has reported 87 percent protection and a 95 percent reduction in ova production by administration of tick midgut (Opdebeeck et al., 1988). Protection was stimulated by administration of detergent solubilized immunogen, and magnitude of resistance expressed was correlated with bovine major histocompatibility antigens (Wong, J. Y. M. and Opdebeeck, J. P., "Protective Efficacy of Antigens Solubilized From Gut Membranes of the Cattle Tick, *Boophilus microplus*," *Immunology*, 66:149–155 (1989)). The nature of the composition of the protection inducing immunogen(s) has not been described.

Significant levels of resistance to infestation with adult *A. americanum* were induced with microgram quantities of tick gut enriched for brush border fragments, or the 27,000 g supernatant from which brush border fragments were separated (Wikel, S. K. "Immunological Control of Hematophagous Arthropod Vectors: Utilization of Novel Antigens," *Veterinary Parasitology*, 29:235–264 (1988)). Mean engorgement weights of ticks from immunized host groups were reduced by up to 69.8 percent, as many as 71.5 percent of challenge ticks were killed and up to 50 percent of viable females did not produce ova.

Sera produced from immunized and control animals were used to identify candidate immunogens by immunoblotting (Wikel, S. K., "Immunological Control of Hematophagous Arthropod Vectors: Utilization of Novel Antigens," *Veterinary Parasitology*, 29:235–264 (1988)). Lectins, peanut agglutinin and wheat germ agglutinin, and immunized host antibodies bound extract components with similar molecular weights on blots of one dimensional sodium dodecyl sulfate polyacrylamide gradient gels. These latter attempts as reported by the inventor in 1988 represent a step along the way; however, they reported less than satisfactory blood spectrum immunity and in some instances the vaccinated mammal showed an adverse skin response to tick feeding caused by secondary cutaneous infection.

To date, in spite of many attempts, there has not yet been developed a successful protocol method and vaccine for immunizing domestic animals against widespread tick infestation. As can be seen from the above description, there is a real and continuing need for a method of selecting and isolating in pure form useful immunogens, for development of protocols for extraction of successful immunogens, and for the development of vaccines containing those immunogens. This invention has as its primary objective the fulfilling of this need.

SUMMARY OF THE INVENTION

A tick vaccine containing an immunogen capable of inducing immunity to tick infestation is prepared from pathogen free tick species or cell lines derived from either tick digestive tract gut cells, preferably brush border or from cells of developing tick larvae. The immunogen is further characterized in that it has a cross reactive, positive immune response to both antibody immunoblotting and to cell mediated immune response of sera of the species to be inoculated. Preferably, the immunogen is in substantially pure homogeneous form. The vaccine form preferably contains at least one immunogen with a pharmaceutically acceptable carrier, adjuvant, immunopotentiator, or diluent which is nonharmful to the mammal to be vaccinated, and at the same time does not denigrate the antibody response to the immunogen.

DETAILED DESCRIPTION OF THE INVENTION

While many sources of pathogen-free ticks can be used as a starting point, a pathogen-free colony of *A. americanum* has been maintained in the inventor's laboratory for eleven years, and was used for the tests here described. These ticks originated from the U.S. Livestock Insects Laboratory, U.S. Department of Agriculture, Kerrville, Tex. These ticks are maintained according to the procedures outlined by Wikel, S. K., "Acquired Resistance To Ticks. Expression of Resistance by C4 Deficient Guinea Pigs," *American Journal of Tropical Medicine and Hygiene*, 28:586–590 (1979), which is incorporated by reference. Female ticks removed from experimental and control hosts for use here were evaluated in regard to the following parameters: viability, engorgement weight, duration of feeding, production of ova, conversion of blood meal weight to ova and viability of ova as determined by percentage which yield larvae. Post-infestation viability of male ticks is determined. Immune responses were tested with randomly bred male Hartley and Strain-13 guinea pigs which are purchased from commercial breeders. Animals are housed in individual cages in rooms maintained at 22° C. with a light/dark illumination cycle of 12 hours each. Commercial diet is fed ad libitum, and water is constantly available. Guinea pig blood is drawn from the dorsal tarsal vein. This procedure and any other that could cause discomfort is performed with use of appropriate tranquilizing drug or anesthesia.

It is important that the ticks used to make the immunogen for vaccine use be pathogen-free. Otherwise pathogen transfer may occur during the vaccination process. Preferably, the ticks should have been demonstrated as pathogen-free for several generations.

Guinea pig infestation with *A. americanum* was performed by restricting ticks to host ears by use of 25 millimeter diameter capsules held in place with thin strips of porous adhesive tape. A thin plastic collar is used to prevent host grooming. Any alterations in tick feeding, reproduction and viability can readily be attributed to host immune effector elements, since grooming is prevented.

Male BALB/c mice were used for generation of antibody producing cells for production of hybridomas. Mice are maintained and fed under conditions similar to those described for guinea pigs.

The immediately following protocol description describes the inventor's protocol as used in both separation of fractions and purification of the same, as well as the immunization regimens, fraction enrichments of derived membranes, electrophoresis characterization of fractions, immunoblotting and cell blots, chromatofocusing and preparation of monoclonal antibodies. Not all of these steps of separation and protocol of testing are always required, but are here set forth for completeness. The important fact is derivation from pathogen-free ticks, separation of immune responsive fractions, preferably in substantially pure form, with the separated fractions providing both positive response to immunoblotting and cell mediated response to sera of the host which is to be vaccinated.

Immunization Regimens

The fractionation to obtain the immunogen can be conducted as below described. Every fraction obtained at each purification step is preferably screened for its ability to induce anti-tick immunity. This process requires weeks in order to assess the impact of induced host resistance on tick biology. However, it is the only presently known way to evaluate a cell fraction in terms of the desired objectives. Each fraction is administered to six (this is a minimum sample size) guinea pigs at a concentration of ten micrograms per 250 grams body weight. As purification proceeds, the relative amount of protection inducing immunogen should increase in this dosage. Immunizations are administered on days 0, 14, 21 and 28 with tick challenge initiated on day 35. Positive immune responses mean the fraction is maintained and used for further processing.

Adjuvant administered at a weight equal to that of immunogen is administered to the mammalian host. In the tests here it is the synthetic double stranded polyribonucleotide complex polyadenylic acid and polyuridylic acid, Poly A: Poly U (Johnson, A. G., "Modulation of the Immune System By Synthetic Polynucleotides,"

*Springer Seminars in Immunopathology*, 2:149–168 (1979)). Both host antibody and cell mediated responses to tick immunogens have been observed by the principal investigator after immunization with this adjuvant. However, as below described, other pharmaceutical carriers can be used as well. An alternative means of enhancing host immune responsiveness is use of the immunostimulating complex, ISCOM, containing the adjuvant Quil A and immunogen (Morein, et al., "The ISCOM: An Immunostimulating Complex," *Immunology Today*, 8:333–338 (1987)).

Impact of host resistance on tick biology is assessed by determination of tick viability, engorgement weight, duration of feeding, production of ova, percent conversion of blood meal weight to ova and viability of ova as determined by percentage which yield larvae.

Enrichment of Tick Digestive Tract Membranes

The method of initial enrichment of tick gut absorptive surface membranes is that of Houk et al., "Isolation and Characterization of Brush Border Fragments From Mosquito Mesenterons," *Archives of Insect Biochemistry and Physiology*, 3:135–146 (1986). This technique was developed for isolation of mosquito mesenteron brush border fragments, but has been found to work for ticks as well.

In this isolation technique, unfed female and male *A. americanum* are surface sterilized by a sequence of rinses in 0.5 percent sodium hypochlorite, one percent benzalkonium chloride, 70 percent ethanol and several changes of distilled water. Ticks are submerged in isolation buffer consisting of 100 mM Tris-HCl, pH 7.2, 300 mM mannitol. Digestive tracts are placed into isolation buffer and homogenized in a glass tissue grinder. Suspension is brought to 10 mM calcium chloride, vortexed and held on ice. Pellet is disrupted in isolation buffer, adjusted for calcium chloride concentration and centrifuged as described. Supernatents obtained from both centrifugations are combined and centrifuged at 27,000 g for 30 minutes at 4° C. Pellet is resuspended in 0.10M Tris-HCl, pH 7.4, 0.15M NaCl. All buffers contain 0.1 mM of the protease inhibitor phenylmethylsulfonyl floride, PMSF. Membrane rich pellet and soluble supernatant are obtained by further centrifugation at 109,544 g for 60 minutes at 4C., using a Beckman TLA 100.3 rotor and TL 100 ultracentrifuge. Final pellet is suspended in the Tris-HCl buffer just described. Samples are stored at −70° C. Protein is determined by the dye-binding assay of Bradford, M. M., "A Rapid And Sensitive Method for Quantitation of Microgram Quantities of Protein Utilizing the Principle of Protein Dye-Binding," *Analytical Biochemistry*, 72:248–254 (1976).

Detergent Solubilization

Integral membrane proteins are removed from molecular association with lipids and individually dispersed into solution by use of non-ionic detergents (Helenius and Simons, "Solubilization of Membranes By Detergents," *Biochimica et Biophysica Acta*, 415:29–79 (1975)). Two non-ionic detergents used in these studies are Triton X-100 and Triton X-114 (Brodier, C., "Phase Separation of Integral Membrane Proteins in Triton X-114 Solution," *Journal of Biological Chemistry*, 256:1604–1607 (1981)). After extraction at 0° C. for 60 minutes with Triton X-100 or Triton X-114, different purification processes are followed. Ultracentrifugation at 109,544 g of Triton X-100 solubilized integral membrane proteins is performed at 4° C. for 60 minutes, with resultant supernatant used for further purification.

Triton X-114 extraction is followed by an elevation in temperature to produce micelles of increasing size (Brodier (1981) supra.) Temperature at which micelles aggregate and come out of solution, cloud point, for Triton X-114 is 20° C. Triton X-114 membrane extract is warmed to 30° C., and after low speed centrifugation integral membrane protein is recovered in detergent rich pellet, while aqueous phase contains soluble proteins.

Another non-ionic detergent that could be used in this system is octylglucoside, which has a high critical micelle concentration and forms small micelles (Thomas and McNamee, "Purification of Membrane Proteins," *Methods in Enzymology*, 182:499–520 (1990)). Ionic detergents are avoided due to subsequent chromatofocusing step, which relies on separation of molecules based on isoelectric point.

Electrophoresis

One and two dimensional polyacrylamide gel electrophoresis are used to characterize fractions obtained during each purification step. One dimensional sodium dodecyl sulfate polyacrylamide gel electrophoresis, SDS-PAGE, is performed according to the method of Laemmli, U. K., "Cleavage of Structural Proteins During Assembly of the Head of Bacteriophage T4," *Nature* 227:680–685 (1970)), using gradient gels designed to cover a broad molecular weight range. Two dimensional gel electrophoresis is performed with nonequilibrium pH gradient electrophoresis in the first dimension and SDS-PAGE in the second (O'Farrell et al, "High Resolution Two-Dimensional Gel Electrophoresis of Basic as Well as Acidic Proteins," *Cell*, 12:1133–1142 (1977)). Isoelectric focusing is effective at resolving molecules with isoelectric points over a pH range of 4 to 7, while nonequilibrium pH gradient electrophoresis resolves molecules across the entire pH range. All gels are silver stained according to the procedure of Morrissey, J. H., "Silver Stains for Proteins in Polyacrylamide Gels: A Modified Procedure With Enhanced Uniform Sensitivity," *Analytical Biochemistry*, 117:307–310 (1981).

Protein concentrations are determined in the absence of detergent by dye-binding assay of Bradford, M. M., "A Rapid And Sensitive Method for Quantitation of Microgram Quantities of Protein Utilizing the Principle of Protein Dye-Binding," *Analytical Biochemistry*, 72:248–254 (1976). Bicinchoninic acid protein assay is used for samples containing non-ionic detergent (Smith, et al., "Measurement of Protein Using Bicinchoninic Acid," *Analytical Biochemistry*, 150:76–85 (1985)).

Immunoblots And Lectin Blots

Protein immunoblotting is performed with sera obtained from protectively vaccinated hosts, animals not protected against tick challenge by immunization and unimmunized, infested controls. Immunogen fractions are separated by SDS-PAGE, electroeluted to nitrocellulose and immunoblotting is performed as previously described (Wikel and Whelen, "Ixodid-Host Immune Interaction. Identification And Characterization of Relevant Antigens And Tick Induced Host Immunosuppression," *Veterinary Parasitology*, 20:149–174 (1986)). Dilution of first antibody is determined by enzyme linked immunosorbent assay (Voller et al., "Enzyme Immunoassays With Special Reference to ELISA Techniques," *Journal of Clinical Pathology*, 31:507–520 (1978). Bound peroxidase labelled secondary antibody probes are localized with the precipitable substrate 4-chloro-1-naphthol.

Lectin blots are prepared from electrophoretograms run and transferred to nitocellulose in a manner similar to that described for immunoblots. Unoccupied protein binding sites are blocked with one percent bovine serum albumin in 0.15M phosphate buffered saline, pH 7.2, 0.05 percent Tween-20. Biotinylated lectins are used to detect appropriate carbohydrate groups and bound lectins are localized by use of horseradish peroxidase conjugated Avidin D (Wikel, S. K., "Immunological Control of Hematophagous Arthropod Vectors: Utilization of Novel Antigens, *Veterinary Parasitology*, 29:235-264 (1988)). Biotinylated lectins with the following specificities are used: concanavalin A binding D-mannose; wheat germ agglutinin binding N-acetyl-D-glucosamine; soybean agglutinin binding N-acetyl-d-galactosamine; peanut agglutinin binding D-galactose and *Ulex europaeus* agglutinin I binding L-fucose residues.

Lectin Affinity Chromatography

Immobilized lectins have been used to obtain high resolution separations of membrane glycoconjugates (Lotan, R. and Nicolson, G. L., "Purification of Cell Membrane Glycoproteins: Lectin Affinity Chromatography," *Biochimica et Biophysica Acta*, 559:329-376 (1979)). Candidate lectins for affinity separation are determined by examination of immunoblots, "cell blots" and lectin blots. Lectin-agarose conjugates are equilibrated with the sample buffer, containing detergent if required. Immobilized glycoconjugates are eluted by appropriate monosaccharides over a range of concentrations, since affinity of glycoconjugates for a given lectin can vary considerably. Sugars used for elution can be removed by dialysis against sample buffer or by Sephadex G-25 chromatography.

Cell Blots

Electrophoretograms identical to those used for immunoblots and lectin blots are electroeluted to nitrocellulose, cut into strips, solubilized, sterilized and used for in vitro stimulation of lymphocytes obtained from experimental and control animals (Young and Lamb, "T-Lymphocytes Respond To Solid Phase Antigen: A Novel Approach To the Molecular Analysis of Cellular Immunity," *Immunology*, 59: 167-171 (1986)). Immunogen bearing particles are diluted to establish a dose response curve. Cell proliferation is evaluated at the fifth day of culture by incorporation of methyltritiated-thymidine. Lymphocyte in vitro culture methods were described by George et al., "Acquisition and Expression of Resistance by *Bos indicus* X *Box taurus* Calves To *Amblyomma Americanum* Infestation," *Journal of Parasitology*, 71:174-182 (1985). This assay allows the screening of individual polypeptides for ability to induce lymphocyte proliferation.

Gel Filtration High Performance Liquid Chromatography

Separation based on molecular size is the next step in purification of protection inducing fractions resulting from lectin affinity chromatography or directly after ultracentrifugation. Gel filtration high performance liquid chromatography provides excellent resolving power, reproducibility and speed. Isocratic fractionation is performed with a Beckman TSK 3000SW column, 7.5 millimeters by 30 centimeters. This column can be operated over a pH range of 2.0 to 7.5 and can resolve globular proteins over a molecular weight range of 1.0 to 150.0 kilodaltons, kdal. This column is operated at a pressure of 500 pounds per square inch at a flow rate of 0.5 milliliter per minute. Column is compatible with non-ionic detergents used in these studies.

Chromatofocusing

Gel filtration derived fractions that stimulate host resistance to infestation are further fractionated by chromatofocusing, allowing for separation of polypeptides into fractions with peak widths of 0.04 to 0.05 pH units (Sluyterman and Elgersma, "Chromatofocusing: Isoelectric Focusing on Ion-Exchange Columns. I. General Principles," *Journal of Chromatography* 150:17–30 (1978); Sluyterman and Wijdenes, "Chromatofocusing: Isoelectric Focusing On Ion-Exchange Columns. II. Experimental Verification," Journal of Chromatography 150:31–44 (1978)). A pH gradient is generated by allowing buffer initially adjusted to one pH to flow through an ion exchange column at another pH. Polypeptides elute from the column at their isoelectric points. Pharmacia chromatofocusing reagents used are Polybuffer 96, pH range 9 to 6; Polybuffer 74, pH range 7 to 4; and Polybuffer exchanger, PBE 94. Chromatofocusing above pH 9 can be performed using Pharmalyte pH 8 to 10.5 and Polybuffer exchanger, PBE 118. One dimensional gels, SDS-PAGE, are used to analyze chromatofocusing derived samples.

Monoclonal Antibodies

If desired to produce monoclonal antibodies to the immunogens here fractionated, those can be generated by conventional means of inducing the fractions obtained by chromatofocusing. In this instance, the fraction polypeptides are separated by SDS-PAGE, recovered from gels, and used to vaccinate animals in order to determine protection inducing capabilities of a band. Immunization and subsequent injection of BALB/c mice for use in monoclonal antibody production was described by Tracy et al., "Development of Monoclonal Antibodies To Proteins Separated By Two-Dimensional Gel Electrophoresis," *Journal of Immunological Methods* 65:97–107 (1983). Booster injections are given and somatic cell fusion is performed three days after last administration of immunogen, according to method of Galfre and Milstein, "Preparation of Monoclonal Antibodies: Strategies And Procedures", *Methods in Enzymology* 73:1–46 (1981). Murine myeloma line used is X63-Ag8.653, which has lost both heavy and light chains. Antibody production is screened by Dot-immunobinding assay (Hawkes et al., "A Dot-Immunobinding Assay for Monoclonal And Other Antibodies," *Analytical Biochemistry* 119:142–147 (1982)). Immunoglobulin purification from ascites is achieved by method of McKinney and Parkinson, "A Simple Nonchromatographic Procedure To Purify Immunoglobulins From Serum And Ascites Fluid," *Journal of Immunological Methods* 96:271–278 (1987).

The following examples, in addition to those earlier set forth in the protocol description above, illustrate the effectiveness of desirable immune response from tick digestive tract or gut cells, preferably brush border surface immunogens.

EXAMPLES OF DIGESTIVE TRACT BRUCH BORDER

Initial induction of resistance to *A. americanum* adults was performed with an extract of unfed gut, enriched for absorptive surface fragments by differential centrifugation. Guinea pigs immunized with this preparation, or the 27,000 g supernatant from which the absorptive surface fragments were purified, did not develop cutaneous hypersensitivity at tick attachment sites upon challenge infestation. Extracts were administered at one microgram per 250 grams body weight for absorptive surface fragments and ten micrograms per 250 grams body weight for 27,000 g supernatant. Levels of resistance induced with absorptive surface fragments were reduction in challenge tick engorgement weight of 69.8 percent, while another group immunized in the same manner allowed challenge ticks to engorge more fully than unimmunized controls. Female *A. americanum* obtaining a blood meal from either immunization group produced fewer viable ova. Ticks harvested from immunized animals, displaying reduced engorgement weights, had 50 percent of females blocked from producing ova, while ticks which fed more fully than those infesting unimmunized controls had 75 percent of females producing viable ova. All ticks survived the challenge infestations.

Vaccination with 27,000 g supernatant from which absorptive surface fragments were prepared contained immunogen, which stimulated significant levels of resistance to challenge infestation. Mean female engorgement weights were reduced by 53.8 to 59.6 percent. Twenty-five to 50 percent of viable female ticks did not produce ova, and 37.5 to 71.5 percent of challenge ticks died. More striking expression of resistance obtained by immunization with 27,000 g supernatant than with brush border fragments could possibly be attributed to dose of antigen rather than intrinsic difference in components present. Both preparations contained membranes, and the one dimensional silver stained sodium dodecyl sulfate polyacrylamide gel patterns of both immunogen preparations were essentially similar.

For each stage of immunogen identification and purification every fraction was screened for protection inducing properties by immunization and tick challenge. Impact of induced resistance was determined by assessment of tick engorgement, ova production and viability.

Purification of absorptive surface fragments included ultracentrifugation at 109,544 g for 60 minutes at 4° C., resulting in a membrane rich pellet and a supernatant containing soluble proteins. Animals were immunized with either 109,544 g pellet or supernatant at a dose of ten micrograms per 250 grams body weight. Each immunogen preparation used in this example was combined with an equal weight of the synthetic polynucleotide adjuvant Poly A; Poly U. A total of three intramuscular injections were given. Other carriers could also be used.

Soluble protein immunized animals developed resistance, which resulted in a mean death rate of 75.0 percent of challenge ticks. Ova production of surviving females was reduced by a mean of 77.3 percent. These findings were unexpected, since it was hypothesized that the most appropriate target for anti-*A. americanum* immunity would be gut absorptive surface integral membrane proteins. Protection inducing soluble protein(s) could be in the digestive cell cytosol.

The 109,544 g pellet, containing tick gut absorptive surface membranes and other membranous elements, induced host anti-tick resistance which caused a mean of 58.0 percent of challenge ticks to die. Females, which obtained a blood meal from ultracentrifugation pellet immunized animals and survived, had ova production reduced by a mean of 68.7 percent. It is quite likely that different protection inducing molecules are present in the ultracentrifugation derived pellet and supernatant.

At each purification step, immune responses of the fraction on control animals are assessed by antibody responses using immunoblotting and by cell mediated immune responses of these animals. The latter by evaluating in vitro responsiveness of lymphocytes. Immunizing fraction of tick gut derived molecules was separated by sodium dodecyl sulfate polyacrylamide gel electrophoresis and electroeluted to nitrocellulose, which was cut into strips containing individual bands. Polypeptide strips were solubilized with dimethylsulfoxide and washed with medium prior to being used in vitro to stimulate lymphocytes derived from immunized or control animals. This technique combined with antibody immunoblotting allowed for a more complete mapping of immunoreactive extract components.

Sera of animals vaccinated with absorptive surface fragment enriched preparation or 27,000 g supernatant were used to identify reactive components of the 27,000 g supernatant. Animals immunized with absorptive surface fragments had antibodies that reacted with 113, 125, 133, 137, 148 and 157 kdal polypeptides, while sera of 27,000 g supernatant vaccinated hosts bound 64, 66, 68, 113, 141, 144, 148, 153 and 157 kdal moieties. Antibodies from both immunization groups bound 113, 148 and 157 kdal extract components. Uninfested, unimmunized controls and experimental animals had immunoglobulins that reacted with a 61 kdal polypeptide.

Selected biotinylated lectins reacted with 27,000 g supernatant glycoconjugates, fractionated in a manner identical to that used for immunoblotting. Concanavalin A. bound to D-mannose containing residues over a molecular weight range of 27 to 154 kdal. Wheat germ agglutinin complexed to N-acetyl-D-glucosamine residues with molecular weights between 37 and 140 kdal. Peanut agglutinin reacted with D-galactose containing moieties over a molecular weight range of 30.5 to 144.0 kdal. *Ulex europaeus* agglutinin I bound L-fucose on extract components with a molecular weight range of 37 to 127 kdal.

Immunoblots and lectin blots were compared. Sera obtained from animals in both immunization groups bound to polypeptides of 148 and 157 kdal, and wheat germ agglutinin reacted with similar molecular weight glycoconjugates. Absorptive surface fragment vaccinated animals bound 133 and 137 kdal polypeptides. A 133 kdal glycoprotein reacted with wheat germ agglutinin and peanut agglutinin reacted with a 137 kdal moiety. Sera collected from 27,000 g supernatant vaccinated animals reacted with 64, 66, 68, 141 and 144 kdal glycoconjugates. Wheat germ agglutinin and peanut agglutinin are the first lectins to be used for affinity isolation of tick gut immunogens.

Immunoglobulins of 109,544 g pellet or supernatant vaccinated animals had titers reactive with the sensitizing component at 1:512 to 1:8,192 at determined by enzyme linked immunosorbent assay. Immunoblotting performed with the same sera revealed antibodies reactive with several extract components over a molecular weight range of 65 to 160 kdal. Both extracts elicited delayed skin reactivity in the animals immunized with that preparation. In vitro lymphocyte proliferation, "cell blot" assays, have been performed and reactive fractions were present. Antibody and cell reactivity patterns of immunogen preparations have yet to be compared. Silver stained one dimensional sodium dodecyl sulfate polyacrylamide gels of fractionated 109,544 g pellet and supernatant contained several polypeptides with similar migration patterns. However, these bands could represent different molecules with similar molecular weights. Two dimensional gels with non-equilibrium pH gradient electrophoresis in the first dimension need to be run and immunoblots prepared from the electrophoretograms of these gels.

It is likely that an anti-*A. americanum* commercial vaccine will incorporate multiple protection inducing immunogens, a factor which might enhance efficacy in an outbred population. Both 109,544 g pellet and supernatant are being fractionated to identify molecules that induce anti-tick immunity.

The latest purification step has been the solubilization of 109,544 g membrane containing pellet with non-ionic detergent, either Triton X-100 or Triton X-114, and the subsequent fractionation of solubilized membrane glycoconjugates by lectin affinity chromatography. First lectin used was agarose immobilized wheat germ agglutinin for isolation of molecules containing N-acetyl-D-glucosamine. Immunization with wheat germ agglutinin affinity purified glycoconjugates of tick gut membrane resulted in expression of variable levels of resistance. Only a mean of 41.7 percent of *A. americanum* females recovered from immunized hosts produced ova; however, only 8.3 percent of challenge females died after obtaining a blood meal from immunized animals. Mean engorgement weight was reduced by only 10.2 percent. Antibody titers of glycoconjugate immunized animals reached a maximum of 1:2,048 by enzyme linked immunosorbent assay. Cell mediated reactivity has been determined, and those data were compared with immunoblot findings.

Elution of glycoconjugates from the lectin immobilizing matrix has required use of sugar eluates of increasing molarity. It appears that some gut extract glycoconjugates do not readily dissociate from wheat germ agglutinin agarose. Immobilized peanut agglutinin will be the next lectin used to enrich the population of protection inducing immunogens.

This example illustrates the main objective of identification of immunogens of *A. americanum* gut that induce anti-tick immunity. At every stage of immunogen identification and isolation, each fraction was tested for its ability to induce host resistance to infestation. Immune effector elements of protectively immunized, susceptible immunized and unimmunized, infested control animals were used as probes for immunogen identification. Antibody reactivity is determined by immunoblotting. Cell mediated immune responsiveness was ascertained by in vitro proliferative responses of lymphocytes elicited by exposure to fractionated immunogen extract components. Cell mediated responsiveness in vitro can be determined for B-lymphocytes, T-lymphocytes, and appropriate cell subpopulations. No heightened cutaneous response was seen in the hosts.

Digestive tract tissue dissected from unfed female *A. americanum* were enriched for absorptive surface fragments, prior to centrifugation at 109,544 g for 60 minutes at 4° C. in a Beckman TL-100 ultracentrifuge, using a TLA 100.3 rotor. A membrane rich pellet and soluble supernatant was obtained for further analysis. Integral membrane proteins were solubilized in the presence of non-ionic detergent. Both pellet and supernatant were analyzed for their protection inducing capabilities. Immunoblots and "cell" blots were prepared and checked. Lectin blotting has been performed to identify carbohydrate binding properties of extract components. The first immunogen purification step was lectin affinity chromatography. Appropriate lectins were selected by comparison of data obtained from immunoblots, "cell" blots and lectin blots. If a suitable correlation was not obtained from examination of extract binding by these probes, the first purification step should be gel filtration high performance liquid chromatography. Subsequent steps in immunogen isolation strategy include gel filtration high performance liquid chromatography, chromatofocusing, generation of monoclonal antibodies to be used for immunoaffinity separation of protection inducing immunogen(s), etc.

EXAMPLES SHOWING SUCCESSFUL ISOLATION OF IMMUNOGEN CELLS FROM DEVELOPING LARVA OF IXODID TICKS

As earlier mentioned, the cells for development of the immunogen can be derived from either tick brush border surface cells or from developing larva of ixodid ticks.

Primary in vitro culture cells of developing *Amblyomma americanum* larvae were administered subcutaneously to guinea pigs at one million cells on days zero, seven and 21. A significant degree of resistance to challenger infestation with *A. americanum* females and males was induced (Wikel, S. K., "Resistance To Ixodid Tick Infestation Induced By Administration of Tick Tissue Culture Cells," *Annals of Tropical Medicine and Parasitology* 79:513–518 (1985)). Mean engorgement weight of female *A. americanum* feeding on vaccinated animals was reduced 74.8 percent and 54.6 percent of female ticks died. All ticks obtaining a blood meal from first exposure hosts were viable. Oviposition by viable females, which fed upon tick cell immunized animals, was reduced by 54 percent, when compared to females engorging on tick susceptible, uninfested, hosts.

Animals immunized with primary culture cells derived from developing larva of *A. americanum* were not only resistant to *A. americanum,* but they also displayed resistance to *D. andersoni* infestation (Wikel, 1985, supra). Mean engorgement weight of female *D. andersoni* was reduced by 70.9 percent for animals feeding upon *A. americanum* larval cell immunized animals, when compared with ticks obtaining a blood meal from first exposure, tick susceptible, controls. This cross protection could be interpreted as indicating the presence of broadly shared epitopes, which are the targets of anti-tick immunity induced by immunization with cells derived from developing larvae of *A. americanum.*

Fertilized, engorged females from the pathogen-free tick collection were collected upon detachment from New Zealand white rabbits. Each engorged female was cleaned by rinsing in three percent hydrogen peroxide, followed by rinses in 70 percent ethanol and distilled water. Each female was stored in a sterile cotton-plugged glass vial in a desiccator over a saturated solution of potassium nitrate, which generates an atmosphere with a relative humidity of approximately 85 percent.

Ova used for the production of in vitro cultures were collected on the tenth day after initiation of egg laying. Methods for preparation of cultures and medium formulation are those described by Yunker and Meibos (1979). Ova from two to five ticks are pooled and dispersed in acetone. Eggs are washed twice and soaked for ten minutes in White's solution, followed by thorough rinsing with sterile distilled water. Eggs are transferred to a 60 millimeter diameter sterile, polystyrene tissue culture dish, and final rinse solution is removed with a Pasteur pipette. Two to three milliliters of growth medium were added to the eggs. Egg shells were cracked by applying gentle pressure with the flat end of a sterile glass rod. An additional seven to eight milliliters of growth medium were placed into the culture dish. A ten milliliter syringe with a 16 gauge needle was used to gently draw up and down the material in the culture dish. This step helps to dissociate tissues of the developing larvae. Final suspension was drawn up into the syringe, and the needle was replaced with a Nucleopore filter holder containing a disc of sterile 16xx silk. Suspension was gently forced through the silk into a sterile conical 15 milliliter polystyrene centrifuge tube. This step reduced the amount of egg shell debris in the final culture. Cells were centrifuged for ten minutes at 150 g at a temperature ranging from 4° C. to room temperature. Supernatant was removed and replaced with ten milliliters of fresh growth medium in which the cells were resuspended. This washing step was repeated twice. Cells were resuspended in ten milliliters of growth medium after the final wash, and five milliliters of cell suspension was placed into each of two 25 centimeter squared polystyrene tissue culture flasks. Cells were incubated in room atmosphere at 27° C. Every seventh day approximately one-half of the growth medium was removed from each flask and fresh medium added. Cells were divided and expanded into new flasks as growth increases.

Immunization

Cells were collected from cultures by centrifugation at 150 g for ten minutes at 4° C., and washed five times with 0.15M phosphate buffered saline, pH 7.2. Centrifugation between washing was performed as just described. Cells were counted and suspended at a concentration of one million cells in 500 microliters 0.15M phosphate buffered saline, pH 7.2, prior to storage at $-20°$ until used.

Guinea pigs were immunized with one million cells, without adjuvant on days zero, seven and 21. Cells were administered in a volume of 500 microliters as a divided subcutaneous dose between two sites on the back. Tick challenge occured on day 35 of this regimen. Magnitude of induced resistance was assessed by evaluation challenge tick engorgement weight, egg production and viability. No heightened cutaneous response was seen in the hosts.

The protection inducing cells can be identified and isolated by the use of antibodies from animals displayed anti-tick immunity after vaccination with tissue culture cells derived from developing larvae. Immunomagnetic separation of cells can be performed using superparamagnetic monodisperse polystyrene particles coated with antibodies specific to the immunogen, direct method, or by a secondary immunoglobulin, indirect method (Funderud et al., "Fractionation of Lymphocytes By Immunogenic Beads", *Lymphocytes. A Practical Approach*, 66 B. Klaus, (Ed) IRL Press Oxford, pp. 55-65, 1987).

Tosylactivated M-450 Dynabeads were coated with affinity purified goat anti-guinea pig immunoglobulins obtained from a commercial supplier. Antibodies from guinea pigs protectively vaccinated with tissue culture cells of developing tick larvae were allowed to react in vitro with ixodid cells. Anti-immunoglobulin coated beads are allowed to react with primary antibody coated cells for 30 minutes at 4° C. with gentle rolling of the suspension. Cell-bead suspension was exposed to a cobalt-samarium magnet for 30 seconds, and unbound cells were decanted. This population of cells was depleted of the protection inducing elements of developing larvae. A bead to cell ratio of 2:1 is used. After 16 to 20 hours of post-isolation incubation, beads release from the cell surface. Detached beads are isolated by exposure to magnetic field and decanting of isolated cells. Growth medium used for these steps should not contain fetal calf serum.

For this example as well as the previous ones for tick brush border cells, the dosage range of cells for each immunization can vary widely. It can be safe to assume that as few as 100,000 cells could induce animal protection. There appears to be no theoretical upper limit, and one could if desired used up to 1 billion cells.

Generally speaking, the number of cells per dose will be within the range of from $10^5$ to $10^8$, and the frequency of dosing will be from two to four times with each injection in a volume of 100 microliters to one milliliter.

The above illustrations show effective development of immunity in host guinea pigs which are representative of the animals for which such vaccines can be used. Other tests have demonstrated a high degree of correlation between guinea pig tests and tests for other domesticated animals such as dogs, cats, cattle, etc. Moreover, the testing has also confirmed that there is a high degree of cross-correlation between genus and species for ticks. That is to say the tick digestive tract brush border cells and developing larvae cells of one tick species will also develop a desired host immune response for other tick species.

While not wishing to be bound by any theory, it is believed that similar techniques to those herein described can be used for developing successful vaccines for other arthropods, such as stable flies, horn flies, black flies, tsetse flies, poultry mites, mange mites and lice. Put another way, it is reasonable to expect that the experiences with ticks, a known arthropod can be carried over to these other arthropods. It is therefore contemplated that such vaccines would also be within the scope of the present invention.

It is also important to note that other tick antigens derived from pathogen-free ticks besides those of tick gut cells, preferably brush border and those of developing larvae, may be used provided they induce the desired immune response, and avoid induction of host cutaneous hypersensitivity to tick feeding. An example of the latter is tick salivary glands who give heightened cutaneous sensitivity and are therefore not good for commercial vaccine use. However, female reproductive tract cells may work as well as gut brush border and larvae cells.

Again, while not wishing to be bound by theory, it is believed that tick cells other than salivary cells work best because these are cells the host animal is not normally subjected to and as a result the host animal is very susceptible to a good immune response.

What is claimed is:

1. An immunogen comprising an antigen which is capable of inducing immunity to tick infestation of a host animal, said immunogen comprising:
   (a) an immunogen isolated and purified from a pathogen-free Amblyomma tick species or cell line;
   (b) said immunogen being isolated and purified from tick cells of a tick digestive tract or from developing tick larva cells and being one which results in a mean death rate of at least 75% of challenged ticks; and (c) said immunogen being one which does not induce host cutaneous hypersensitivity to tick feeding and one which provides a cross reactive positive immune response involving both antibody and cell mediated immune response for sera and cells of the species to be inoculated.

2. The immunogen of claim 1 which is derived from tick brush border cells.

3. The immunogen of claim 1 which is derived from developing tick larva cells.

4. The immunogen of claim 1 wherein said immunogen provides a positive immune response at each step of isolation and purification.

5. A tick vaccine comprising an immunogen which is capable of inducing immunity to tick infestation of host animals, said vaccine comprising, in combination:
   (a) an immunogen isolated and purified from a pathogen-free Amblyomma tick species or cell line;
   (b) said immunogen being isolated and purified from tick cells of a tick digestive tract or from developing tick larva cells and being one which results in a mean death rate of at least 75% of challenged ticks;
   (c) said immunogen being one which does not induce host cutaneous hypersensitivity to tick feeding and one which provides a cross reactive positive immune response involving both antibody and cell mediated immune response for sera and cells of the species to be inoculated; and
   (d) a pharmaceutically acceptable tick vaccine carrier which is both non-harmful to the animal to be vaccinated and which does not negatively impact on the immune response of said immunogen.

6. The vaccine of claim 5 wherein the immunogen is derived from tick brush border cells.

7. The vaccine of claim 5 wherein the immunogen is derived from developing tick larva cells.

8. The vaccine of claim 5 wherein the immunogen comprises a mixture of immunogen derived from tick brush border cells and from developing tick larva cells.

9. The vaccine of claim 5 wherein said pharmaceutically acceptable carrier is selected from the group consisting of adjuvants, immunopotentiators and diluents.

10. The tick vaccine of claim 5 wherein said immunogen at each step of isolation and purification provides a positive immune response.

11. A method of immunizing a host animal against tick infestation, said method comprising inoculating said host animal with a vaccine containing an immunogen which is capable of inducing immunity to tick infestation, said immunogen comprising:
    (a) an immunogen isolated and purified from a pathogen-free Amblyomma tick species or cell line;
    (b) said immunogen being isolated and purified from tick cells of a tick digestive tract or from developing tick larva cells and being one which results in a mean death rate of at least 75% of challenged ticks; and
    (c) said immunogen being one which does not induce host cutaneous hypersensitivity to tick feeding and one which provides a cross reactive positive immune response involving both antibody and cell mediated immune response for sera and cells of the species to be inoculated.

12. The method of claim 11 wherein said immunogen is in substantially pure homogeneous form.

13. The method of claim 11 wherein said immunogen is a mixture of immunogens derived from tick brush border cells and/or developing tick larva cells.

14. The method of claim 11 wherein said vaccination is intramuscularly.

15. The method of claim 11 wherein said vaccination is subcutaneously.

16. The method of claim 11 wherein said host mammalian species is selected from the group consisting of cattle, horses, dogs, cats, rabbits, guinea pigs, and swine.

17. The method of claim 11 wherein at each step of isolation and purification, the immunogen is checked for positive immune response and further processed only if it provides positive immune response.

18. The method of claim 13 wherein the immunogen is derived from digestive track brush border.

19. The method of claim 11 wherein the immunogen is derived from developing tick larvae cells.

20. The method of claim 11 wherein the immunogen is in substantially pure form.

21. The method of claim 11 wherein at each step of isolation and purification said immunogen provides a positive immune response.

* * * * *